United States Patent [19]

Sugden

[11] Patent Number: 4,717,723
[45] Date of Patent: Jan. 5, 1988

[54] PHARMACEUTICAL COMPOSITIONS

[75] Inventor: Keith Sugden, Beverly, Great Britain

[73] Assignee: Reckitt & Colman Products Limited, London, Great Britain

[21] Appl. No.: 785,544

[22] Filed: Oct. 8, 1985

[30] Foreign Application Priority Data

Oct. 16, 1984 [GB] United Kingdom ............... 8426152

[51] Int. Cl.⁴ .............................................. A61K 31/54
[52] U.S. Cl. .................................... 514/224; 514/223; 514/974
[58] Field of Search ................... 424/80; 514/223, 224

[56] References Cited

U.S. PATENT DOCUMENTS

| 2,407,486 | 9/1946 | Flenner et al. | 514/223 |
| 3,218,232 | 11/1965 | Stein et al. | 514/223 |
| 4,559,326 | 12/1985 | Crawford et al. | 514/224 |

FOREIGN PATENT DOCUMENTS

| 1108376 | 4/1968 | United Kingdom | 424/80 |
| 1531987 | 11/1978 | United Kingdom | 424/80 |

Primary Examiner—Frederick E. Waddell
Attorney, Agent, or Firm—Bacon & Thomas

[57] ABSTRACT

Pharmaceutical compositions in the form of a buccal tablet comprise a phenothiazine derivative, at least one monosaccharide or disaccharide or a mixture thereof, and a mixture of xanthan gum and locust bean gum in a weight ratio of 3:1 to 1:1. A particular buccal tablet containing prochlorperazine maleate affords improved bioavailability.

10 Claims, 1 Drawing Figure

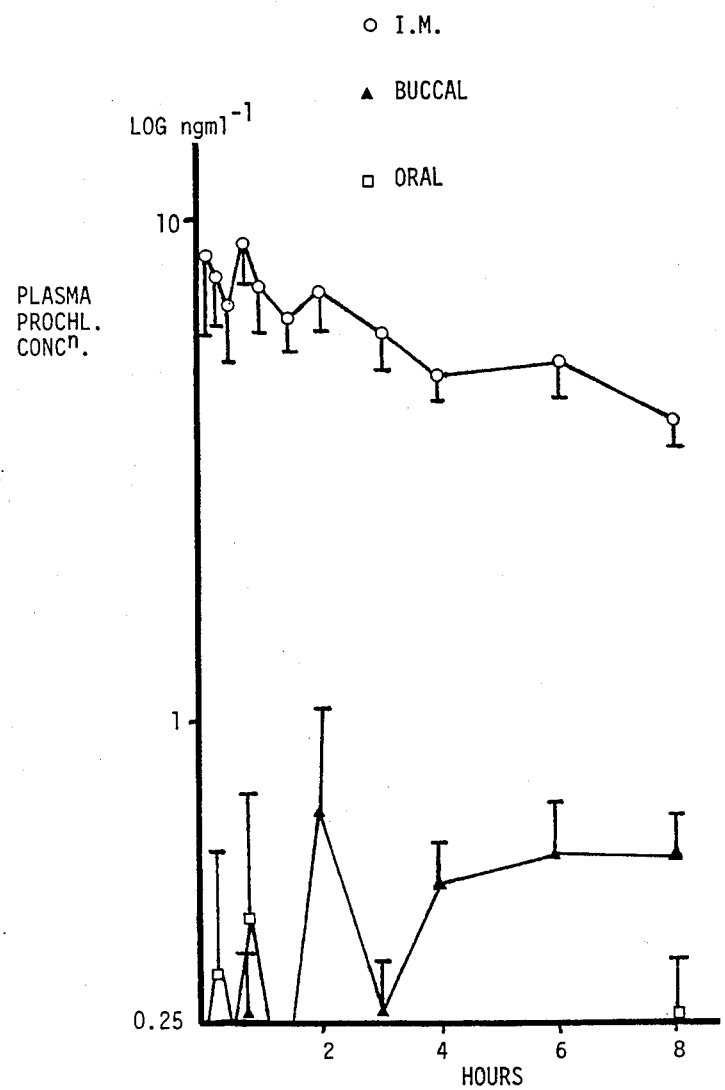

PHARMACEUTICAL COMPOSITIONS

This invention relates to pharmaceutical compositions and in particular to compositions containing phenothiazines and especially prochlorperazine.

Prochlorperazine (INN for 2-chloro-10-[3-(4-methylpiperazin-1-yl)propyl]phenothiazine) in the form of its salts is used in the control of nausea and vomiting. It is also used in the treatment of vertigo. Prochlorperazine as the free base is a liquid somewhat sensitive to light. In liquid preparations whether for parenteral administration or in the form of a syrup for oral administration the drug is used in the form of its mesylate salt. In tablets it is the maleate salt which is employed.

In investigations in human volunteers, we have found that blood levels of the drug following the swallowing of a conventional tablet are somewhat variable from person to person and are only of the order of 4% of that found following parenteral administration. There is evidence that higher blood levels can be obtained from a sublingual formulation which is held below the tongue. However because of the bitter taste of the drug and a local anaesthetic effect a sublingual tablet is unacceptable to patients.

We have now developed a buccal tablet which affords blood levels several times higher than those to be found when a tablet is swallowed and which avoids the disadvantages associated with the presentation of prochlorperazine by the sublingual route.

According to this invention there is provided a buccal tablet comprising prochlorperazine maleate, at least one monosaccharide or disaccharide or a mixture thereof, and a mixture of xanthan gum and locust bean gum in a weight ratio of 3:1 to 1:1.

Suitable monosaccharides include glucose, galactose, fructose, mannose, mannitol and sorbitol. The disaccharides include maltose, lactose and sucrose, a preferred carrier being sucrose.

The tablets will normally contain 3 to 10 mg prochlorperazine maleate and conveniently 5 mg.

The total weight of the mono- and/or di-saccharides relative to the combined weight of the xanthan and locust bean gums is conveniently in the ratio of 20:1 to 5:1 and preferably in the ratio of 16:1 to 7.5:1.

In an aspect of this invention there is provided a buccal tablet comprising (a) a phenothiazine derivative selected from
1. those having a dimethylaminopropyl sidechain such as chlorpromazine hydrochloride, methotrimeprazine hydrochloride or
2. those having a piperidine sidechain such as pericyazine, piperacetazine, or
3. those having a piperazine sidechain such as acetophenazine maleate, butaperazine maleate, fluphenazine hydrochloride, perphenazine, prochlorperazine maleate, thiethylperazine maleate, thiopropazate hydrochloride, thioproperazine mesylate, trifluoperazine hydrochloride; (b) at least one monosaccharide or disaccharide or a mixture thereof; and (c) a mixture of xanthan gum and locust bean gum in a weight ratio of 3:1 to 1:1.

The total weight of the mono- and/or di-saccharides relative to the combined weight of the xanthan and locust bean gums is conveniently in the ratio of 20:1 to 5:1 and preferably in the ratio of 16:1 to 7.5:1.

The locust bean gum is preferably a cold-water dispersible type such as Meyprodyn 200 (Registered Trade Mark, Meyhall Chemical A.G., Switzerland).

The tablets will preferably contain granulating and disintegrating agents such as starch, binding agents such as polyvinylpyrrolidone, lubricating agents such as magnesium stearate and/or glidants such as talc.

The tablets are prepared by standard tabletting procedures in which various components are blended together and the mixture directly compressed or else there is a pregranulation stage using for example a wet granulation with isopropanol followed by the tabletting.

The buccal tablets of the present invention are placed between the gingival surface of the jaw and the buccal mucosa where they gel by water absorption to produce a soft hydrated tablet which may be retained in position giving prolonged and controlled release of the drug by diffusion for upto two hours.

The invention is illustrated by the following Examples.

EXAMPLE 1

Buccal tablets (60 mg) having the composition

|  | mg |
| --- | --- |
| xanthan gum (Keltrol F, Kelco, USA) | 1.5 |
| locust bean gum (Meyprodyn 200) | 1.5 |
| prochlorperazine maleate | 5.0 |
| polyvinylpyrrolidone (Kollidon K30 BASF) | 3.0 |
| sucrose (Dipac, Amstar Corp, USA) | 47.5 |
| magnesium stearate | 0.5 |
| talc | 1.0 | were prepared by blending together all the components except for the talc and magnesium stearate. The mixed powders were then wet granulated using isopropanol using a planetary mixer, the damp granules being passed through a 750 $\mu$m sieve and then dried at 50° C. After drying the mass was passed through a 500 $\mu$m sieve, blended with the talc and magnesium stearate and compressed into 5.56 mm diameter, normal concave profile tablets of nominal weight 60 mg and breaking strength 2–5 Kp using a rotary tablet press.

EXAMPLES 2–4

Buccal tablets (50 mg) were prepared having the composition:

|  | mg |
| --- | --- |
| xanthan gum (Keltrol F) | x |
| locust bean gum (Meyprodyn 200) | y |
| prochlorperazine maleate | 5.0 |
| magnesium stearate | 0.5 |
| talc | 0.1 |
| sucrose (Dipac) | 43.5 − (x + y) | where x and y are respectively

| Example | 2 | 3 | 4 |
| --- | --- | --- | --- |
| x = | 1.5 | 2.5 | 2.25 |
| y = | 1.5 | 2.5 | 0.75 |

The dry powders were screened through a 750 $\mu$m sieve before being thoroughly blended. The mixed powders were compressed on a single punch tablet press using 4 mm diameter normal concave punches at a compression load of 2–2.5 KN to produce tablets of nominal weight 50 mg.

EXAMPLE 5

Buccal tablets (50 mg) having the composition:

|   | mg |
|---|---|
| xanthan gum (Keltrol F) | 1.5 |
| locust bean gum (Meyprodyn 200) | 1.5 |
| prochlorperazine maleate | 5.0 |
| magnesium stearate | 0.5 |
| talc | 1.0 |
| lactose B.P. | 40.5 | were prepared by the method of Example 2.

EXAMPLE 6

Buccal tablets (50 mg) having the composition:

|   | mg |
|---|---|
| xanthan gum (Keltrol F) | 1.5 |
| locust bean gum (Meyprodyn 200) | 1.5 |
| prochlorperazine maleate | 5.0 |
| magnesium stearate | 0.5 |
| talc | 1.0 |
| anhydrous dextrose B.P. | 40.5 | were prepared by the method of Example 2.

EXAMPLE 7

The composition of the tablets of Example 1 was varied by replacing the sucrose by 47.5 mg mannitol B.P. The tablets of nominal weight 60 mg had breaking strength of 2-5 Kp.

EXAMPLE 8

Buccal tablets (60 mg) were prepared having the composition:

|   | mg |
|---|---|
| sucrose (Dipac) | 26.25 |
| mannitol | 26.25 |
| locust bean gum (Meyprodyn 200) | 1.5 |
| xanthan gum (Keltrol F) | 1.5 |
| prochlorperazine maleate | 3.0 |
| magnesium stearate | 0.5 |
| talc | 1.0 |

The dry powders were screened through a 750 μm sieve before being thoroughly blended. The mixed powders were compressed on a single punch tablet press using 5.56 mm diameter normal concave punches at a compression load of 2-4 KN to produce tablets of nominal weight 60 mg.

EXAMPLE 9

Buccal tablets similar to those of Example 8 were prepared using sorbitol (Sorbit Instant, E. Merck, W. Germany) in place of the mannitol.

EXAMPLE 10

Buccal tablets (60 mg) were prepared by the method of Example 8 having the composition:

|   | mg |
|---|---|
| sorbitol (Sorbit-Instant) | 52.5 |
| locust bean gum (Meyprodyn 200) | 1.5 |
| xanthan gum (Keltrol F) | 1.5 |
| prochlorperazine maleate | 3.0 |
| magnesium stearate | 0.5 |
| talc | 1.0 |

EXAMPLE 11

Buccal tablets similar to those of Example 10 were prepared using fructose (Tabfine F94M, Suomen Sokeri OY, Finland) in place of the sorbitol.

EXAMPLE 12

Buccal tablets (60 mg) were prepared by the method of Example 8 having the composition:

|   | mg |
|---|---|
| sucrose (Microtal DCE, Tate & Lyle, GB) | 46.25 |
| locust bean gum (Meyprodyn 200) | 4.625 |
| xanthan gum (Keltrol F) | 4.625 |
| prochlorperazine maleate | 3.0 |
| magnesium stearate | 0.5 |
| talc | 1.0 |

EXAMPLE 13

Buccal tablets (60 mg) were prepared by the method of Example 8 having the composition:

|   | mg |
|---|---|
| sucrose (Dipac) | 50.45 |
| locust bean gum (Meyprodyn 200) | 2.525 |
| xanthan gum (Keltrol F) | 2.525 |
| prochlorperazine maleate | 3.0 |
| magnesium stearate | 0.5 |
| talc | 1.0 |

EXAMPLE 14

Buccal tablets similar to those of Example 12 were preared using sorbitol (Sorbit Instant) in place of the sucrose.

EXAMPLE 15

Buccal tablets (60 mg) were prepared by the method of Example 8 having the composition:

|   | mg |
|---|---|
| sucrose (Dipac) | 45.5 |
| locust bean gum (Meyprodyn 200) | 1.5 |
| xanthan gum (Keltrol F) | 1.5 |
| chlorpromazine hydrochloride | 10.0 |
| magnesium stearate | 0.5 |
| talc | 1.0 |

EXAMPLE 16

Buccal tablets similar to those of Example 15 were prepared using thiethylperazine hydrogen maleate (10 mg) in place of the chlorpromazine hydrochloride.

COMPARATIVE EXAMPLES A-D

Buccal tablets (50 mg) were prepared according to the method of Examples 2-4 and having a similar composition in which x and y are respectively

| Example | A | B | C | D |
|---------|-----|-----|------|---|
| x =     | 3.0 | 0.0 | 0.75 | 0 |
| y =     | 0.0 | 3.0 | 2.25 | 0 |

The tablets of the present invention have been evaluated in in-vitro and in-vivo tests.

The in-vitro release rate of the buccal tablets was investigated using a method based on British Pharmacopaeia 1980, Volume II, A114. Tablets were placed in a standard wire gauze basket (Copley Instruments (Nottingham) Ltd.) and rotated at 100 rpm in 100 ml of 0.1M phosphate buffer (pH 6.7) contained in a 150 ml tall form beaker, placed in a water bath maintained at 37±1° C. At intervals 1 ml aliquots were removed and diluted to 5 or 10 ml volumes with distilled water, the aliquot being replaced by 1 ml buffer. The sample solutions were assayed for prochlorperazine maleate content by direct UV measurement at 254 nm in a 1 cm (3 ml volume) quartz UV cell using a Perkin-Elmer 552 spectrometer.

Table 1 presents data on the tablets of Examples 2 to 4 and Comparative Examples A to D.

TABLE 1

| Example No. | Description | t50% (hr) | Survival time (hr) |
|---|---|---|---|
| 2 | 1.5 mg Xn/1.5 mg Mn (1:1) | 12.7 | >22 |
| 3 | 2.5 mg Xn/2.5 mg Mn (1:1) | 13.4 | >22 |
| 4 | 2.25 mg Xn/0.75 mg Mn (3:1) | 14.6 | >23 |
| A | 3 mg Xn | 8.3 | >23 |
| B | 3 mg Mn | <0.1 | <0.25 |
| C | 0.75 mg Xn/2.25 mg Mn (1:3) | 0.4 | <1.5 |
| D | No gum | 0.1 | <0.17 |

Xn = Xanthan gum;
Mn = Meyprodyn gum;
t50% = time for tablet content to fall to 50%;
survival time = longest inspection time at which tablet structure was still evident.

From the results it can be seen that tablets containing xanthan gum alone (3 mg) showed considerably slower release than tablets containing locust bean gum (3 mg Meyprodyne gum) which disintegrated very rapidly as did tablets containing no gum at all. A mixture of xanthan gum and locust bean gum in a ratio of 1:1 or 3:1 produced slower release than xanthan gum alone on a weight for weight basis, but a mixture of 1:3 gave a very rapid release.

Non-invasive in-vivo studies were carried out on the buccal tablets in volunteers by the following procedure:

A single tablet was placed between the upper gingival surfaces of the jaw and buccal mucosa of the cheek pouch of each volunteer, the same position being used on each occasion a tablet was taken. The tablet was held in the mouth without disturbance for a specified period before removal of the residue. Analysis for the total amount of drug remaining in the tablet was carried out by an hplc method. Assay by the hplc procedure was carried out after removing the tablet from the mouth to a 25 ml beaker, adding 10 ml of 9:1 methanol/conc.HCl, ultrasonicating until dissolved and diluting to 25 ml in a volumetric flask with distilled water. The solutions were filtered through a folded 11 cm No. 4 filter paper (Whatman, Registered Trade Mark) into a 8 dram vial and 20 μl aliquots were taken for assay. Chromatography was carried out on a 10×0.46 cm Partisil ODS-2 column using a acetonitrile/water/concentrated sulphuric acid (30/70/0.01 v/v) mobile phase delivered at 2 ml/minute. Detection was at 254 nm using a Cecil CE212 UV spectrophotometer (0.1 a.u. FSD). The percentage of the drug content remaining was calculated by reference to the total tablet content for each tablet batch.

The percentage retention of drug within the tablet matrix was assessed in three volunteers after holding the tablet in the buccal area for 0.5, 1 or 2 hours. Results are set out in Table 2.

TABLE 2

| Example No. | Time | % Drug content remaining in Volunteers | | | |
|---|---|---|---|---|---|
| | | 1 | 2 | 3 | Mean |
| 2 | 1.0 | 54.0 | 42.6 | 39.3 | 45.3 |
| (3 mg gum mixture) | 2.0 | 30.1 | 35.4 | 0 | 21.8 |
| 3 | 1.0 | 80.6 | 40.2 | 67.7 | 62.8 |
| (5 mg gum mixture) | 2.0 | 61.7+ | 76.1 | 23.9* | 53.9** |

+1.5 hours;
*1.83 hours: tablet slipped onto tongue before 2 hours, removed and assayed;
**mean time 1.78 hr Tablets containing xanthan/Meyprodyn gum mixtures gelled in the mouth by water absorption, as observed in-vitro, to give a soft tablet which adhered to the buccal mucosa and consequently remained in position for up to two hours. Tablets containing none of the gum mixture did not gel, but tended to remain in position as the table wetted, however when fully hydrated the tablet disintegrated to produce a smear of particles on the gingivae and cheek. The relative bioavailability of prochlorperazine following parenteral, oral or buccal administration to six volunteers has been studied. In the evaluation the patients received one of the following treatments.

1. Two buccal tablets of Example 1, each containing 5 mg prochlorperazine maleate and 3 mg xanthan gum:-locust bean gum (1:1) in a sucrose base, the tablets being placed on either side of the upper gum over the molar teeth area held in position until dissolved.

2. Two oral tablets of Stemetil (Registered Trade Mark, May & Baker Ltd., Dagenham, UK) each containing 5 mg prochlorperazine maleate, swallowed with 100 ml water.

3. Stemetil injection (May & Baker Ltd) 1 ml containing 12.5 mg prochlorperazine mesylate given intra-muscularly over five seconds.

Blood samples (10 ml) were taken at intervals up to 8 hours after administration. After collection the specimens were centrifuged and the plasma transferred to clean acid washed silanized glass tubes for prochlorperazine determinations according to the following procedures.

Five ml plasma was pipetted into a test tube and 75 μl 0.316 ngml$^{-1}$ internal standard, 1 ml 1.0M sodium hydroxide solution and 8 ml diethylether:chloroform (4:1) mixture added. The sample was stoppered, mixed on a vortex stirrer for one minute and centrifuged at 2000 rpm for five minutes. The upper organic layer was transferred by Pasteur pipette into a clean 10 ml tube and evaporated to dryness under a stream of nitrogen. The organic residue was reconstituted in 75 μl of the chromatographic mobile phase and a 50 μl aliquot assayed by high performance liquid chromatography (hlpc) carried out on a 25×0.46 cm stainless steel column packed with Spherisorb-CN (Phase Sep, Deeside Industrial Estate, Queensferry, Clwyd, UK). The mobile phase consisted of 0.1M Dipotassium hydrogen phosphate solution, adjusted to pH 6.5 with $H_3PO_4$, acetonitrile and methanol (7:6:4 v/v) delivered at a rate of 2.0 ml/min$^{-1}$. The eluant was monitored by an electrochemical detector fitted with a glassy carbon electrode and operated with an applied potential of 0.75 V in the oxidation mode at a range of 2 nanoamperes. The detector output was connected to a Hewlett Packard reporting integrator.

A summary of the mean plasma prochlorperazine concentrations is shown in FIG. 1.

Plasma concentrations after oral and buccal administration were markedly reduced compared with the i.m. route. In five of the volunteers the plasma prochlorperazine levels following oral dosing were substantially lower than those following buccal administration and in two subjects the plasma levels following the oral dose were too low to be determined at any time point.

It is calculated from these studies that the mean bioavailability for the buccal routes increases by at least 2 fold over that of the oral route.

We claim:

1. A buccal tablet comprising an effective amount in the control of nausea, vomiting, or in the treatment of vertigo of prochlorperazine maleate, at least one monosaccharide, disaccharide or a mixture thereof, and a mixture of xanthan gum and locust bean gum in a weight ratio of 3:1 to 1:1, and wherein the total weight of the mono- and/or disaccharides relative to the combined weight of the xanthan and locust bean gums is in the ratio of 20:1 to 5:1.

2. A buccal tablet as claimed in claim 1 wherein the weight of prochlorperazine maleate is between 3 mg and 10 mg.

3. A buccal tablet as claimed in claim 1, wherein the monosaccharide is glucose, galactose, fructose, mannose, mannitol or sorbitol.

4. A buccal tablet as claimed in claim 1, wherein the disaccharide is maltose, lactose or sucrose.

5. A buccal tablet as claimed in claim 1 wherein the total weight of the mono- and/or di-saccharides relative to the combined weight of the xanthan and locust bean gums is in the ratio of 16:1 to 7.5:1.

6. A buccal tablet as claimed in claim 2 wherein the monosaccharide is glucose, galactose, fructose, mannose, mannitol or sorbitol.

7. A buccal tablet as claimed in claim 2 wherein the disaccharide is maltose, lactose or sucrose.

8. A buccal tablet as claimed in claim 2 wherein the total weight of the mono- and/or di-saccharides relative to the combined weight of the xanthan and locust bean gums is in the ratio of 16:1 to 7.5:1.

9. A buccal tablet as claimed in claim 3 wherein the total weight of the mono- and/or di-saccharides relative to the combined weight of the xanthan and locust bean gums is in the ratio of 16:1 to 7.5:1.

10. A buccal tablet as claimed in claim 4 wherein the total weight of the mono- and/or di-saccharides relative to the combined weight of the xanthan and locust bean gums is in the ratio of 16:1 to 7.5:1.

* * * * *